United States Patent [19]
Verduin, Jr.

[11] Patent Number: 5,501,667
[45] Date of Patent: Mar. 26, 1996

[54] PERFUSION BALLOON AND METHOD OF USE AND MANUFACTURE

[75] Inventor: Kenneth L. Verduin, Jr., Coral Springs, Fla.

[73] Assignee: Cordis Corporation, Miami Lakes, Fla.

[21] Appl. No.: 213,150

[22] Filed: Mar. 15, 1994

[51] Int. Cl.⁶ ................................................ A61M 29/02
[52] U.S. Cl. ........................... 604/96; 604/101; 606/194
[58] Field of Search .................. 604/96–103, 51–53, 604/280–283; 606/191–194

[56] References Cited

U.S. PATENT DOCUMENTS

| | | |
|---|---|---|
| 3,889,686 | 6/1975 | Duturbure . |
| 4,183,102 | 1/1980 | Guiset . |
| 4,233,983 | 11/1980 | Rocco . |
| 4,423,725 | 1/1984 | Baran et al. . |
| 4,447,227 | 5/1984 | Kotsanis . |
| 4,581,017 | 4/1986 | Sahota . |
| 4,585,000 | 4/1986 | Hershenson . |
| 4,641,653 | 2/1987 | Rockey . |
| 4,694,827 | 9/1987 | Weiner et al. . |
| 4,723,549 | 2/1988 | Wholey et al. . |
| 4,762,130 | 8/1988 | Fogarty et al. . |
| 4,763,653 | 8/1988 | Rockey . |
| 4,771,777 | 9/1988 | Horzewski et al. . |
| 4,787,388 | 11/1988 | Hofmann . |
| 4,790,315 | 12/1988 | Mueller, Jr. et al. . |
| 4,795,427 | 1/1989 | Heizel . |
| 4,820,271 | 4/1989 | Deutsch . |
| 4,832,028 | 5/1989 | Patel . |
| 4,857,054 | 8/1989 | Helfer . |
| 4,877,031 | 10/1989 | Conway et al. . |
| 4,878,495 | 11/1989 | Grayzel . |
| 4,892,519 | 1/1990 | Sponger et al. . |
| 4,909,252 | 3/1990 | Goldberger . |
| 4,983,167 | 1/1991 | Sahota . |
| 5,000,734 | 3/1991 | Boussignac et al. . |
| 5,000,743 | 3/1991 | Patel . |
| 5,006,119 | 4/1991 | Acker et al. . |
| 5,019,042 | 5/1991 | Sahota . |
| 5,035,694 | 7/1991 | Kasprzyk et al. . |
| 5,046,503 | 9/1991 | Schneiderman . |
| 5,078,685 | 1/1992 | Colliver . |
| 5,087,247 | 2/1992 | Horn et al. . |
| 5,090,958 | 2/1992 | Sahota . |
| 5,090,960 | 2/1992 | Don Michael . |
| 5,108,370 | 4/1992 | Wallinsky . |
| 5,129,883 | 7/1992 | Black . |
| 5,135,474 | 8/1992 | Swan et al. . |
| 5,137,513 | 8/1992 | McInnes et al. . |
| 5,147,377 | 9/1992 | Sahota . |
| 5,152,277 | 10/1992 | Honda et al. . |
| 5,160,321 | 11/1992 | Sahota . |
| 5,181,911 | 1/1993 | Shturman . |
| 5,195,955 | 3/1993 | Don Michael . |
| 5,195,971 | 3/1993 | Sirhan . |
| 5,222,941 | 6/1993 | Don Michael . |
| 5,226,888 | 7/1993 | Arney . |
| 5,232,446 | 8/1993 | Arney . |
| 5,261,879 | 11/1993 | Brill . |
| 5,295,959 | 3/1994 | Gurbel et al. . |
| 5,295,995 | 3/1994 | Kleiman . |
| 5,304,135 | 4/1994 | Shonk .................... 604/101 |
| 5,308,323 | 5/1994 | Sogawa et al. .......... 604/101 X |
| 5,342,301 | 8/1994 | Saab .......................... 604/96 |

*Primary Examiner*—John D. Yasko
*Attorney, Agent, or Firm*—Lockwood, Alex, Fitzgibbon & Cummings

[57] ABSTRACT

A dilation catheter suitable for use in medical procedures is provided. The catheter includes a balloon disposed on an elongated tube. The tube is capable of passing fluid between the balloon and the tube for varying the balloon between an inflated expanded condition and a deflated collapsed condition. The balloon includes a longitudinally extending septum which cooperates with the exterior skin of the balloon to separate the balloon into a plurality of substantially equally sized chambers. The septum further cooperates with the balloon to form at least one longitudinally extending channel disposed outwardly of the exterior surface between adjacent chambers of the balloon. The channels allow blood to be perfused past the balloon when the balloon is disposed in a body vessel in its expanded condition.

23 Claims, 1 Drawing Sheet

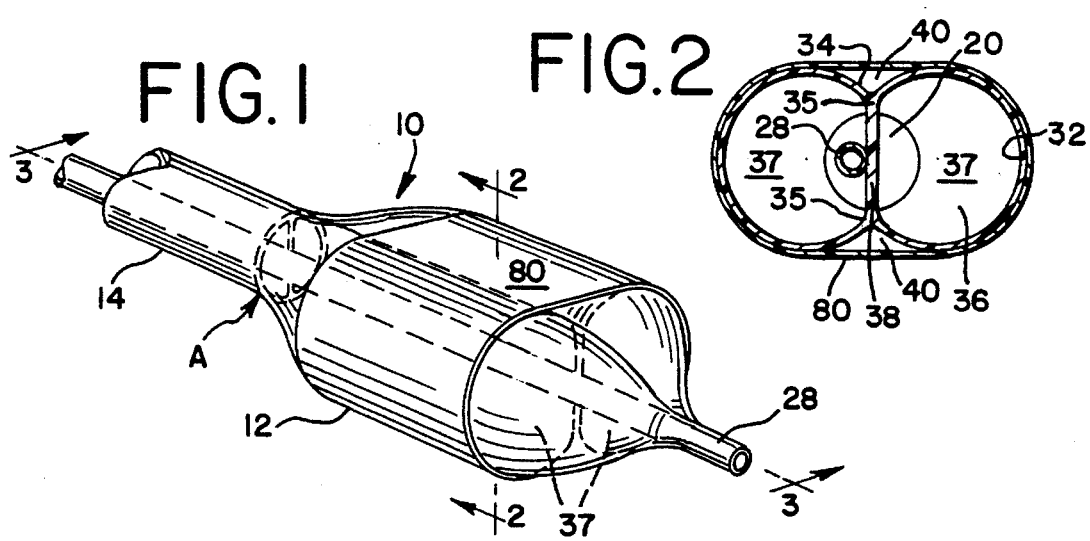
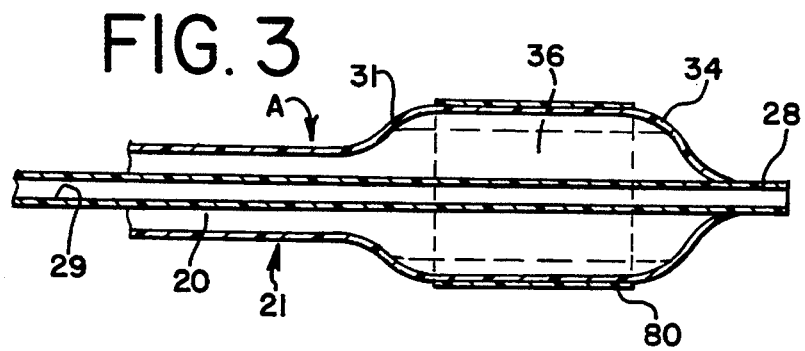
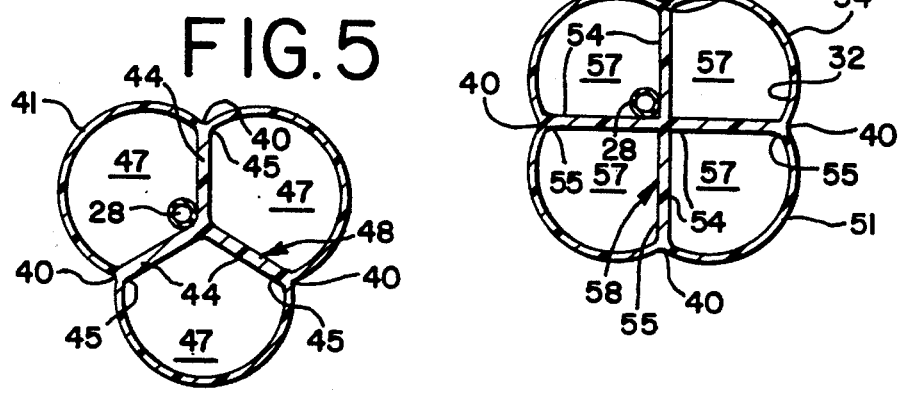

PERFUSION BALLOON AND METHOD OF USE AND MANUFACTURE

The present invention relates generally to dilation catheters suitable for percutaneous transluminal coronary angioplasty procedures (PTCA), and more particularly to dilation catheters for use in PTCA procedures wherein blood is perfused distally of the dilation balloon during the inflation cycle of the balloon.

BACKGROUND AND SUMMARY OF THE INVENTION

PTCA procedures generally include inflation of a balloon in an arterial passage in an effort to clear a flow path for blood by dilating the stenosis. Inflation of the balloon and subsequent deflation and removal of the balloon results in treatment of the stenosis to increase the available cross-sectional area for blood to flow through the arterial passage.

In typical PTCA procedures, a guiding catheter is inserted into the cardiovascular system through the Tee-brachial or femoral arteries, generally under local anesthesia, until the distal tip of the catheter is in a coronary artery and generally positioned adjacent a stenosis. An extensible balloon of a dilation catheter is advanced through the guiding catheter alone or over a previously introduced guidewire until the balloon is positioned across the stenosis. The balloon is then inflated to a predetermined size with a fluid, preferably a radiopaque liquid, to radially compress the inside of the artery wall, thereby dilating the lumen of the artery. The balloon is then deflated so that the dilation catheter can be removed, and blood flow resumed through the dilated artery that now has a larger cross-sectional area to permit a greater volume of blood to flow therethrough.

In typical PTCA procedures, when the balloon of a dilation catheter is inflated in a coronary artery, all flow ceases through the coronary artery. If blood flow ceases for too long a period of time, the part of the heart and associated sidebranches which that coronary artery serves can begin to suffer from lack of blood, or ischemia. If the balloon remains inflated in the artery for prolonged periods of time, the injury caused by the absence of blood flow can be irreversible in some cases. On the other hand, it has been found that the probability of an artery wall or the stenosis maintaining its dilated cross-sectional area after having been subjected to dilation from an extensible balloon is directly related to the length of time that the balloon is inflated while located across the stenosis. However, the aforementioned potential problems associated with blocking blood flow are increased the longer the balloon is inflated in the artery.

Attempts have been made to produce dilation catheters that perfuse blood through a catheter or balloon when the balloon is inflated to avoid ischemia conditions distally of the balloon. For example, Wijay, et al., U.S. Pat. No. 5,158,540, disclose a perfusion catheter that perfuses blood during the balloon's inflation cycle to allow for longer inflation periods; however, the catheter is extremely complicated structurally and expensive to manufacture.

It is, therefore a general object of the present invention, to provide a new and improved perfusion balloon dilation catheter suitable for PTCA procedures.

Another object of the invention is to provide a dilation catheter suitable for PTCA procedures wherein the catheter perfuses blood around the inflated balloon and permits prolonged inflation times for the balloon.

Yet another object of the present invention is to provide a dilation catheter of a relatively simple structure for use in PTCA procedures where blood is perfused distally of the inflated balloon.

Another object of the present invention is to provide a dilation catheter having a multichambered balloon that forms longitudinally extending channels when inflated which are designed to perfuse blood around the inflated balloon when it is inflated in vivo.

The present invention overcomes the problems associated with the prior art perfusion catheters by providing a perfusion balloon catheter having a multichamber balloon member with an exterior and interior surface disposed on a flexible tubular member. The multichamber balloon includes a longitudinally extending member common to at least two of these chambers which defines and separates the chambers and cooperates with the exterior surface of the balloon to form longitudinally extending channels outwardly from the exterior surface between adjacent chambers. The balloon may be varied between a collapsed condition of a size allowing the catheter to be transported through a body vessel and an expanded condition of a size allowing the exterior surface to engage a body vessel wall. These longitudinally extending channels allow blood to be perfused past the balloon when the balloon is inflated in a body vessel.

For a complete understanding of the present invention, reference is made to the embodiments illustrated in greater detail in the accompanying drawings and described by way of example. It should be understood that this invention is not limited to the particular embodiments illustrated herein, but is defined by the appended claims.

BRIEF DESCRIPTION OF THE DRAWINGS

FIG. 1 is a perspective view of a portion of a balloon catheter made according to the present invention and shown in its inflated condition;

FIG. 2 is a cross-sectional view through the balloon portion of the catheter of FIG. 1, taken along line 2—2;

FIG. 3 is a longitudinal cross-sectional view of the catheter of FIG. 1, taken along line 3—3;

FIG. 4 is a cross-sectional view of an outlet nozzle of a die of the type utilized to extrude a parison used in forming the balloon of the present invention;

FIG. 5 is a cross-sectional view of a three-chambered balloon according to the present invention;

FIG. 6 is a cross-sectional view of a four-chambered balloon according to the present invention.

DETAILED DESCRIPTION OF THE PREFERRED EMBODIMENT

While the invention may be embodied in a variety of forms and used in different applications such as angioplasty, valvuloplasty, and urological uses, a description of one preferred embodiment of the inventive concept will be made in the form of a dilation catheter for use in percutaneous transluminal coronary angioplasty procedures. As illustrated in the drawings, the perfusion balloon catheter, generally designated at 10 in FIG. 1, made according to the present invention comprises an extensible multichamber balloon 12 located substantially near the distal end of an elongated flexible tubular shaft 14. The catheter may include a hub (not shown), of a type well known in the art. Any suitable fitting and/or hub can be provided as desired. It should be understood that the present invention may be used on fixed-wire, over-the-wire, and monorail type balloon catheters, for example.

As shown in FIGS. 1 through 3, an annular lumen 20 is located within tubular shaft 14. Lumen 20 is utilized for carrying fluid, such as radiopaque saline solution or other fluid of a type well known in the art. The fluid carried by lumen 20 is communicated to balloon 12 for inflating and deflating balloon 12. It should be understood that the diameter of lumen 20 is large enough to carry sufficient amounts of fluid for inflating balloon 12 with sufficient speed to be suitable for angioplasty procedures and the like.

In addition, the annular lumen 20 of flexible tubular shaft 14 is further defined by a second tubular shaft 28, having a lumen 29 which may be of a substantially small diameter similar to that of the outer diameter of a standard guidewire, preferably having a diameter of between about 0.008 inch and about 0.022 inch. As illustrated, lumen 20 is substantially larger in cross-sectional area than lumen 29 so as to facilitate transmission of fluid to and from the balloon. Lumen 29 may be utilized to receive a guidewire to provide assistance in placing the dilation catheter at the appropriate position in a body vessel. It should be understood that lumen 29 extends through the body of the balloon while annular lumen 20 stops at and is sealingly connected to the proximal end of the balloon at the area designated A in FIG. 1. The fluid carried by lumen 20 enters the interior of the balloon generally at 21 (FIG. 2), evenly inflating each chamber of the balloon.

Flexible tubing 14 and 28 utilized in the present invention is preferably formed of a suitable thermoplastic material, such as polyethylene, polyvinylchloride, nylon, polyethylene terephthalate and the like, or from a suitable composite structure. Flexible tubular member 14 and annular lumen 20 end at the proximal end of the balloon while lumen 29 extends through the balloon and is slightly offset from the longitudinal axis of the balloon as shown in FIGS. 2, 5 and 6.

The balloon is generally cylindrically shaped having an exterior skin 31 including an inner surface 32 and an exterior surface 34. The balloon is then sealed about its proximal end to flexible tube 14 and about its distal end to flexible tube 28, defining an interior compartment 36 generally therebetween. The balloon may be inflated to an expanded condition by the introduction of fluid through flexible tube 14 and lumen 20 into interior compartment 36. When fluid is removed from interior compartment 36 the balloon returns to a collapsed condition.

Compartment 36 of the balloon includes a plurality of chambers 37, preferably of substantially equal size, defined by the septum extending longitudinally from the distal end to the proximal end of the balloon. In the dual-chamber embodiment shown in FIGS. 1, 2, and 3, a single uniplanar septum 38 is included, while septums 48 and 58 having multi-walled or multi-planar configurations are shown in FIGS. 5 and 6, respectively. Each such septum is preferably formed integrally with the balloon and is generally substantially thicker in width than the exterior skin 31. By varying the septum configuration, the balloon may include any number of chambers. For example, FIG. 1 shows a two-chamber balloon having chambers 37 separated by septum 38, FIG. 5 shows a three-chamber balloon having chambers 47 separated by septum 48, and FIG. 6 shows a four-chamber balloon having chambers 57 separated by septum 58. Each septum 38, 48, 58 separates and is a common element to each chamber 37, 47, 57 cooperating with the exterior skin to define each said individual chamber. The septum, such as septums 48, 58, may include equally sized radially extending branches 44, 54 having end portions generally corresponding in number to the number of chambers desired. Thus, for example, the balloon illustrated in FIG. 6 is shown with four chambers 57 and four branches 54 and associated end portions 55.

The septum and its branches extend the longitudinal length of the balloon. The end portions 35, 45, 55 of the branches are spaced radially inwardly from the exterior surface and cooperate with the exterior surface to form longitudinally extending channels 40. The exterior surface is also drawn slightly radially inwardly at positions adjacent end portions 35, 45, 55. It should be understood, however, that the septum and its associated branches and end portions as well as the exterior skin of the balloon including the interior surface and exterior surface are formed integrally. The channels 40 are more prominent when the balloon is in its expanded condition and allow blood to be perfused past the inflated balloon prolonging the time the balloon may remain inflated in the body vessel. Channels 40 are more prominent when the balloon is in its expanded state due in large measure to the differences in thicknesses between the exterior skin and septum 38, 48, 58. The thicker septum tends to be less compliant than the thinner exterior skin 31, 41, 51 which extends radially outwardly when inflated, defining a portion of channel 40.

In addition, the balloon may include a membrane 80 or a sheath disposed over the channels and which will extend and collapse, generally together with the balloon, in response to fluid pressure within the balloon. Preferably, the membrane is attached to the outer surface of the balloon, such as by heat sealing the membrane to the body of the balloon, or by utilizing an adhesive. The membrane is utilized to help minimize the filling in of the channel 40 by stenotic material and to help make the angioplasty more uniform.

Balloon 12 is made from a parison that is extruded through an extrusion outlet die 50 illustrated in FIG. 4. Die 50 has a continuous outlet opening 51 including thin arcuate cavity sections 52 for extruding material that will eventually become the exterior balloon skin and a wider thick section 54 separating the parison into chambers through which material will be extruded eventually forming the balloon septum. Although die 50 is shown with two thin arcuate sections for forming chambers separated by a single thick section, any number of equally sized chambers may be formed by utilizing additional radially extending thickened sections to separate each chamber. For example, correspondingly shaped dies are used to form parisons for other balloons such as those shown in FIGS. 5 and 6. Material extruded through the thick sections will eventually become the septum including the branches and end portions.

After molding, the parison typically is subject to blow molding and the like in order to thin down the walls of the parison. Generally speaking, this thinning will be proportional to the wall thickness at a given location along the parison. Thus, in the balloon, the thin arcuate sections will remain functionally thinner than the septum to approximately the same degree as in the parison.

The balloon is to be produced from material that exhibits compliance adequate to expand as discussed herein. Examples include polyethylene, latex rubber, polyvinyl chloride, nylon, polyamide, polyethylene terephthalate, polyurethane or other suitable flexible and somewhat elastic material. Preferably, the material will be at least as compliant as nylons such as Nylon 12.

When the balloon is inflated to its expanded condition by the introduction of fluid into its interior compartment, exterior skin 31 expands radially outwardly from the longitudinal axis of the balloon. When fluid is removed from the interior compartment, interior surface 32 is substantially adjacent the balloon's longitudinal axis, and the balloon is in a substantially collapsed state.

In a typical operation, catheter 10 is generally advanced from the femoral artery or the Tee-brachial artery up the aortic root and is positioned in the appropriate coronary artery or peripheral body vessel. Advancement of the catheter through an artery or body vessel is preferably performed when the balloon is in its collapsed, non-inflated condition. The balloon which is disposed at the distal end of the catheter is positioned across a restriction or stenosis in the artery. Thereafter, the balloon is inflated in the artery by pumping fluid through lumen 20 of flexible tubing 14. Inflation of the balloon causes the balloon to radially expand causing exterior surface 34 to engage the artery wall or stenosis and dilate the artery wall. The balloon may remain in its expanded condition for a considerably longer time than conventional catheters because the blood is perfused past the balloon through longitudinally extending channels 40 without need for a separate mechanism to pump or channel the blood.

When utilizing the catheter 10 made according to the present invention, it may be desirable to rotate the balloon about its longitudinal axis to insure that the entire inner surface of the artery wall or stenosis is engaged by the inflated balloon. The surgeon performing the PTCA procedure would insert the balloon and inflate it as before. This allows the balloon to engage a majority of the inner circumference of the artery wall or stenosis. To ensure that the area of the artery wall not initially engaged by the exterior surface of the balloon is dilated, the balloon is deflated and rotated between approximately 30° to 90° depending on the number of channels 40. The balloon is then reinflated to insure that the portion of the artery wall or stenosis not previously dilated is engaged by the exterior surface 34. The balloon may be deflated, rotated, and reinflated as many times as is necessary.

When utilizing the catheter made according to the present invention, a guidewire typically is first inserted into the body vessel. This can be facilitated when the catheter is of the dual lumen type as discussed herein. The catheter may then be inserted over the guidewire wherein the guidewire extends through lumen 29 to assist in positioning the catheter in the body vessel. After the perfusion catheter has performed its function of dilating the restricted artery or the like, the balloon may be deflated and the catheter removed.

One advantage of the balloon of the present invention is that each of the chambers of the balloon are inflated by a single lumen of the catheter eliminating the need to separately control flow to and from each chamber. Furthermore, the coaxial alignment of annular lumen 20 and septum 38, 48, 58 allows even inflation of each chamber 37, 47, 57.

It will thus be seen that the present invention provides a new and useful perfusion balloon catheter having a number of advantages and characteristics, including those pointed out herein and others which are inherent in the invention. Preferred embodiments of the invention have been described by way of example, and it is anticipated that modifications may be made to the described form without departing from the spirit of the invention or the scope of the appended claims.

What is claimed is:

1. A dilation catheter for use in medical procedures comprising: an elongated flexible tubular member; a unitary multichamber balloon having an exterior surface and being disposed on said tubular member, said unitary multichamber balloon having a collapsed condition of a size allowing said balloon to be transported through a body vessel, and said balloon having an expanded condition of a size allowing said balloon to engage a body vessel wall; a longitudinally extending septum formed integrally with said balloon and coaxial therewith, said septum being generally substantially thicker in width than said exterior surface of said balloon, said septum further including radially extending portions spaced inwardly of said exterior surface and cooperating with said balloon to define a plurality of chambers within said balloon, said septum further cooperating with said balloon to define a longitudinally extending channel exteriorly of and between adjacent chambers of said balloon when said balloon is in its expanded condition; and means for passing fluid between said balloon chambers and said flexible tubular member to evenly vary said balloon between its collapsed and expanded conditions.

2. The dilation catheter of claim 1, wherein said multichamber balloon includes a first chamber and a second chamber separated by said longitudinally extending septum.

3. The dilation catheter of claim 1, wherein said plurality of chambers are equally sized.

4. The dilation catheter of claim 1, wherein said flexible tubular member includes a first lumen for transporting a fluid and a second lumen for receiving a guidewire.

5. The dilation catheter of claim 1, wherein said flexible tubular member includes an inner lumen for receiving a guidewire and an outer lumen for transporting a fluid.

6. The dilation catheter of claim 1, wherein said flexible tube is coaxial with the longitudinal axis of said longitudinally extending septum.

7. The dilation catheter of claim 1, wherein said means for passing fluid between said balloon member and said flexible tubing includes at least one pathway between said flexible tubular member and each chamber of said multichamber balloon.

8. The dilation catheter of claim 4, wherein the proximal end of said balloon is in seal-tight communication with a first tube defining said first lumen and the distal end of said balloon is sealingly connected to a second tube defining said second lumen.

9. The dilation catheter of claim 1, further including a membrane disposed over said longitudinally extending channel, said membrane sealingly connected to the exterior surface of the balloon.

10. The dilation catheter of claim 1, wherein said balloon dimensions increase approximately on the order of three times between its collapsed condition and its expanded condition.

11. The dilation catheter of claim 1, wherein said longitudinally extending septum is a common element to each of the chambers of said multichambered balloon.

12. A method of forming a dilation catheter having a unitary multichamber balloon with a longitudinally extending perfusion channel for perfusing fluid past the balloon when the balloon is disposed in a vessel, said balloon being inflatable between a collapsed condition and an expanded condition, said method comprising: providing an outlet die having a single continuous outlet portion, said outlet portion having at least one narrow section and one wide section; supplying a polymer to said outlet die; extruding a multichambered parison through said outlet die wherein the portion of the polymer extruded through said wide section defines a septum common to each chamber and the portion of the polymer extruded through the narrow section defines an exterior portion of said multichambered parison, said septum being generally substantially thicker in width than said exterior portion of said multichambered parison; blow molding said multichambered parison to form said unitary multichamber balloon; and connecting said balloon in seal-tight communication to the distal end of a flexible tubular member.

13. A dilation catheter for use in medical procedures comprising: an elongated flexible tubular member; a unitary balloon disposed on said tubular member, said unitary balloon having an interior surface and an exterior surface, and said unitary balloon having a collapsed condition of a size allowing said unitary balloon to be transported through a body vessel and an expanded condition of a size allowing said exterior surface of said unitary balloon to engage a body vessel wall; said unitary balloon further including a plurality of equally sized chambers defined by a portion of said exterior skin and a longitudinally extending septum formed integrally with said exterior skin and common to each of said chambers, said septum being generally substantially thicker in width than said exterior surface of said unitary balloon, said septum further being coaxial with said unitary balloon and cooperating with said exterior surface to define at least one longitudinally extending channel disposed outwardly of said exterior surface between adjacent chambers of said unitary balloon when said Unitary balloon is in its expanded condition; and means for passing fluid between said chambers and said flexible tubular member to evenly vary said unitary balloon between its collapsed condition and its expanded condition.

14. The dilation catheter of claim 13, wherein said flexible tubular member includes a first lumen for transporting a fluid and a second lumen for receiving a guidewire.

15. The dilation catheter of claim 13, wherein said flexible tubular member includes an inner lumen for receiving a guidewire and an outer lumen for transporting a fluid.

16. The dilation catheter of claim 13, wherein said flexible tube is coaxial with said longitudinally extending septum.

17. The dilation catheter of claim 13, wherein said means for passing fluid between said balloon member and said flexible tubing includes at least one pathway between said flexible tubular member and each chamber of said multichamber balloon.

18. The dilation catheter of claim 13, wherein the proximal end of said balloon is in seal-tight communication with a first tube defining said first lumen and the distal end of said balloon is sealingly connected to a second tube defining said second lumen.

19. The dilation catheter of claim 13, further including a membrane disposed over said longitudinally extending channel, said membrane sealingly connected to the exterior surface of the balloon.

20. The dilation catheter of claim 13, further including a plurality of longitudinally extending channels.

21. The dilation catheter of claim 13, wherein said septum includes radially extending branches for forming said equally sized chambers.

22. The dilation catheter of claim 21, wherein said radially extending branches traverse the longitudinal extent of said balloon.

23. The dilation catheter of claim 22, wherein said radially extending branches cooperate with said exterior skin to define said longitudinally extending channel disposed outwardly of said exterior surface between adjacent chambers of said balloon.

* * * * *